US012741369B2

(12) United States Patent
Takagi

(10) Patent No.: US 12,741,369 B2
(45) Date of Patent: Sep. 22, 2026

(54) METHOD AND APPARATUS FOR CONTROLLING CONTINUUM ROBOT

(71) Applicants: Kiyoshi Takagi, Tokyo (JP); CANON U.S.A., INC., Melville, NY (US)

(72) Inventor: Kiyoshi Takagi, Tokyo (JP)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 18/841,309

(22) PCT Filed: Feb. 23, 2023

(86) PCT No.: PCT/US2023/013697
§ 371 (c)(1),
(2) Date: Aug. 23, 2024

(87) PCT Pub. No.: WO2023/164047
PCT Pub. Date: Aug. 31, 2023

(65) Prior Publication Data

US 2025/0162134 A1 May 22, 2025

Related U.S. Application Data

(60) Provisional application No. 63/313,995, filed on Feb. 25, 2022.

(51) Int. Cl.

| | |
|---|---|
| ***B25J 9/06*** | (2006.01) |
| ***A61B 1/005*** | (2006.01) |
| ***B25J 9/10*** | (2006.01) |

(52) U.S. Cl.
CPC ............... *B25J 9/065* (2013.01); *B25J 9/104* (2013.01); *A61B 1/0057* (2013.01)

(58) Field of Classification Search
CPC ......... B25J 9/065; B25J 9/104; A61B 1/0057; A61B 1/00006; A61B 1/00148;
(Continued)

(56) References Cited

U.S. PATENT DOCUMENTS

| | | |
|---|---|---|
| 6,201,387 B1 | 3/2001 | Govari |
| 9,144,370 B2 | 9/2015 | Kato et al. |

(Continued)

FOREIGN PATENT DOCUMENTS

| | | |
|---|---|---|
| WO | 2020/194212 A1 | 10/2020 |
| WO | 2021/142272 A1 | 7/2021 |

(Continued)

*Primary Examiner* — Abby Lin
*Assistant Examiner* — Renee LaRose
(74) *Attorney, Agent, or Firm* — Canon U.S.A., Inc., IP Division

(57) ABSTRACT

An apparatus includes a bendable body including at least a distal bending portion and a proximal bending portion, a first driving mechanism for bending the distal bending portion, a second driving mechanism for bending the proximal bending portion, a controller that controls the first driving mechanism to bend the distal bending portion and controls the second driving mechanism to bend the proximal bending portion, and a receiving unit that receives a command on an amount of bending of part or all of the bending portions. The controller is configured to switch between first control for bending only the distal bending portion according to the command received by the receiving unit and second control for bending the distal bending portion and the proximal bending portion so that the distal bending portion and the proximal bending portion have constant curvature according to the command received by the receiving unit.

7 Claims, 18 Drawing Sheets

(58) Field of Classification Search

CPC ... A61B 1/0016; A61B 1/0052; A61B 1/0055; A61B 34/32; A61B 2034/301; A61B 34/71

See application file for complete search history.

(56) References Cited

U.S. PATENT DOCUMENTS

| | | | |
|---|---|---|---|
| 10,687,694 | B2 | 6/2020 | Tanaka et al. |
| 11,007,641 | B2 | 5/2021 | Takagi et al. |
| 11,051,892 | B2 | 7/2021 | Hata et al. |
| 11,096,552 | B2 | 8/2021 | Hata et al. |
| 11,103,992 | B2 | 8/2021 | Tanaka et al. |
| 11,278,366 | B2 | 3/2022 | Kose et al. |
| 11,504,501 | B2 | 11/2022 | Kato et al. |
| 11,559,190 | B2 | 1/2023 | Okumura et al. |
| 11,571,268 | B1 | 2/2023 | Masaki et al. |
| 11,622,828 | B2 | 4/2023 | Kincaid et al. |
| 2007/0135803 | A1 | 6/2007 | Belson |
| 2012/0271109 | A1 | 10/2012 | Belson |
| 2015/0088161 | A1 | 3/2015 | Hata et al. |
| 2018/0243900 | A1 | 8/2018 | Tanaka et al. |
| 2018/0296282 | A1* | 10/2018 | Kose .................... A61B 1/0053 |
| 2018/0311006 | A1 | 11/2018 | Kose et al. |
| 2019/0015978 | A1 | 1/2019 | Takagi et al. |
| 2019/0105468 | A1 | 4/2019 | Kato et al. |
| 2020/0375665 | A1 | 12/2020 | Masaki et al. |
| 2021/0121051 | A1 | 4/2021 | Altshuler et al. |
| 2021/0121162 | A1 | 4/2021 | Ninni et al. |
| 2021/0259521 | A1 | 8/2021 | Hwang |
| 2021/0259790 | A1 | 8/2021 | Kaiser |
| 2021/0259794 | A1 | 8/2021 | Kato et al. |
| 2021/0260339 | A1 | 8/2021 | Ninni |
| 2021/0260767 | A1 | 8/2021 | Masaki et al. |
| 2021/0308423 | A1 | 10/2021 | Kincaid |
| 2021/0362323 | A1 | 11/2021 | Tanaka et al. |
| 2021/0369081 | A1 | 12/2021 | Kose |
| 2021/0369085 | A1 | 12/2021 | Kato et al. |
| 2021/0369355 | A1 | 12/2021 | Masaki et al. |
| 2021/0369366 | A1 | 12/2021 | Hwang et al. |
| 2021/0386972 | A1 | 12/2021 | Chang et al. |
| 2022/0016394 | A1 | 1/2022 | Ninni |
| 2022/0039635 | A1 | 2/2022 | Shia |
| 2022/0039784 | A1 | 2/2022 | Hwang et al. |
| 2022/0040450 | A1 | 2/2022 | Haubert |
| 2022/0126060 | A1 | 4/2022 | Shia et al. |
| 2022/0202273 | A1 | 6/2022 | Ninni |
| 2022/0202277 | A1 | 6/2022 | Chang et al. |
| 2022/0202500 | A1 | 6/2022 | Ninni et al. |
| 2022/0202501 | A1 | 6/2022 | Zhang et al. |
| 2022/0202502 | A1 | 6/2022 | Zhang et al. |
| 2022/0203071 | A1 | 6/2022 | Hwang et al. |
| 2023/0016761 | A1 | 1/2023 | Kaiser et al. |
| 2023/0137954 | A1 | 5/2023 | Hwang et al. |
| 2023/0201522 | A1 | 6/2023 | Hwang et al. |
| 2023/0255442 | A1 | 8/2023 | Masaki et al. |

FOREIGN PATENT DOCUMENTS

| | | | |
|---|---|---|---|
| WO | 2022/031995 | A1 | 2/2022 |
| WO | 2022/032162 | A1 | 2/2022 |
| WO | 2023/150162 | A1 | 8/2023 |
| WO | 2023/154246 | A1 | 8/2023 |
| WO | 2023/154352 | A1 | 8/2023 |
| WO | 2023/154713 | A1 | 8/2023 |
| WO | 2023/154825 | A1 | 8/2023 |
| WO | 2023/154931 | A1 | 8/2023 |

* cited by examiner

Proposed
Base
3rd tip
2nd tip
1st tip
Conventional

METHOD AND APPARATUS FOR CONTROLLING CONTINUUM ROBOT

PRIORITY AND INCORPORATION BY REFERENCE

The present application claims priority to U.S. Provisional Patent Application Ser. No. 63/313,995, filed Feb. 25, 2022 the disclosure of which is hereby incorporated herein by reference in its entirety.

TECHNICAL FIELD

The present disclosure relates to a method and an apparatus for controlling a continuum robot.

BACKGROUND

Continuum robots include a plurality of bending sections with a flexible structure, the shapes of which are controlled by deforming the bending sections. These robots mainly have two superior points over rigid link robots. First, continuum robots are movable along a curve in a narrow space or an environment with scattered objects in which rigid link robots would get caught. Second, continuum robots have substantial flexibility, and can be operated without damaging fragile objects. This does not necessarily need detection of an external force and the like, which is needed for rigid link robots. With these advantages, application to the medical field, such as sheaths for endoscopes and catheters, and ultimate working robots, such as rescue robots, is expected. Patent Document 1 discloses a method of control for a continuum robot used as an endoscope to enter a space. In this case, the bent shape of the forward section is propagated to the following section in all of the adjacent bending sections with the advance of the endoscope base, thereby continuously propagating the shape.

Patent Document 1 STEERABLE ENDOSCOPE AND IMPROVED METHOD OF INSERTION, US2012/271109, BELSON AMIR In Patent Document 1, the shape of the entire continuum robot is controlled in such a manner that the shape of the bending portion at the distal end is propagated to the following portion by operating the target angle of the bending section at the most distal end and the displacement of the base. Bending only the bending portion at the distal end (a distal bending portion) has a problem in that the range in which the distal end of the continuum robot can be moved is limited to the bendable range of only the distal bending portion.

SUMMARY OF THE DISCLOSURE

An apparatus includes a bendable body including at least a first bending portion and a second bending portion, a first driving mechanism for bending the first bending portion, a second driving mechanism for bending the second bending portion, a controller that controls the first driving mechanism to bend the first bending portion and controls the second driving mechanism to bend the second bending portion, and a receiver that receives a command on an amount of bending of part or all of the bending portions. The controller is configured to switch between first control for bending the first bending portion according to the command received by the receiver and second control for bending the first bending portion and the second bending portion so that the first bending portion and the second bending portion have constant curvature according to the command received by the receiver.

This configuration allows switching from control for indicating only the curvature of the distal bending portion to control for linking the plurality of bending sections. The switching according to the situation can increase the range of movement of the distal end of the continuum due to a bending operation.

The above configuration also allows switching from control for linking the plurality of bending sections to control for indicating only the curvature of the distal bending portion. Such switching can reduce the probability of the continuum robot coming into contact with the wall of a tube through which the continuum robot is passed.

BRIEF DESCRIPTION OF THE DRAWINGS

FIGS. 10(*a*) to 10(*e*) are graphs illustrating simulation results according to the first embodiment.

FIGS. 14(*a*) to 14(*e*) are graphs illustrating simulation results according to the second embodiment.

DETAILED DESCRIPTION

First Embodiment

Figure 1:
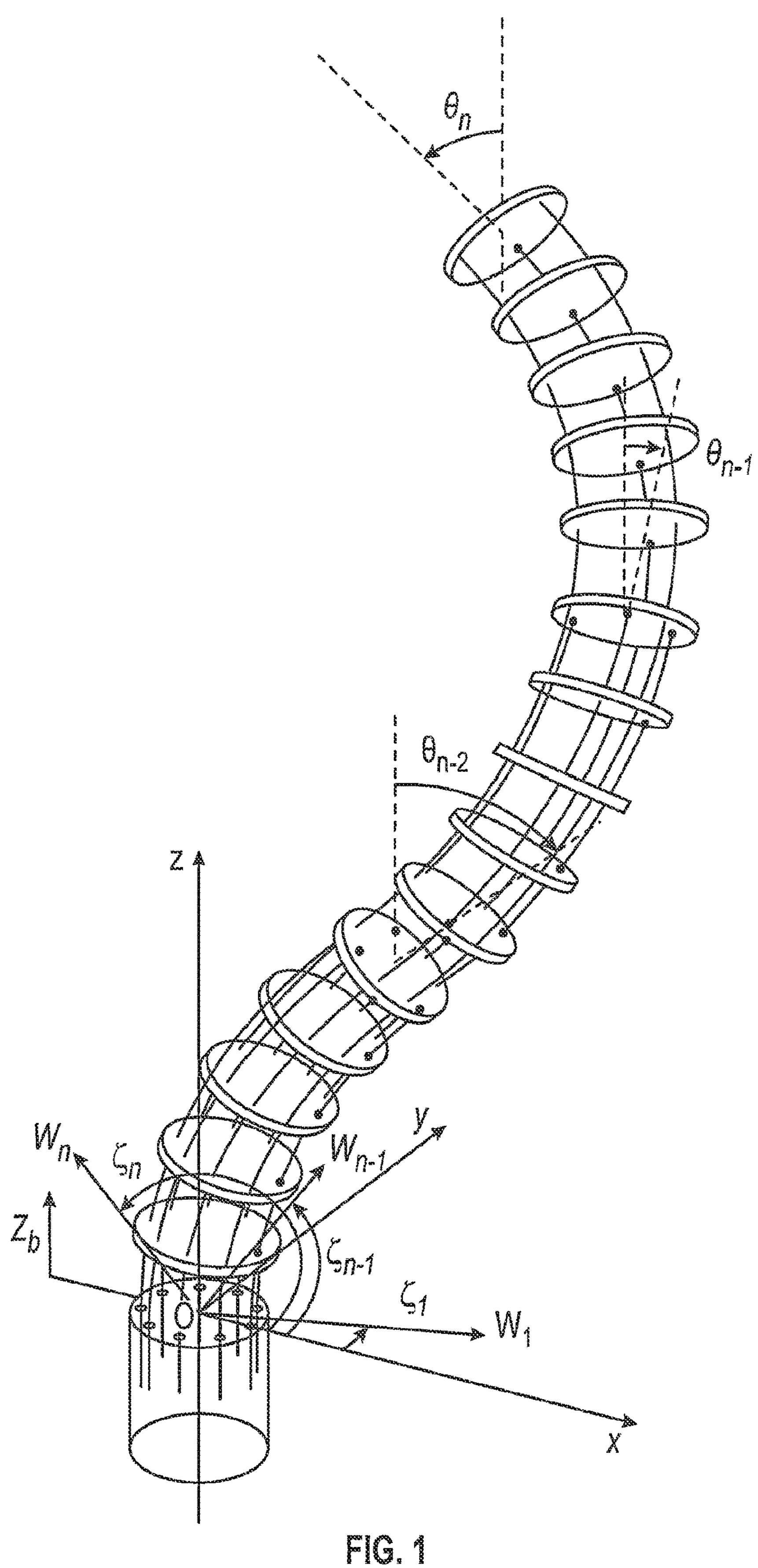
FIG. 1 is a diagram illustrating a kinematic model according to a first embodiment.
Figure 2:
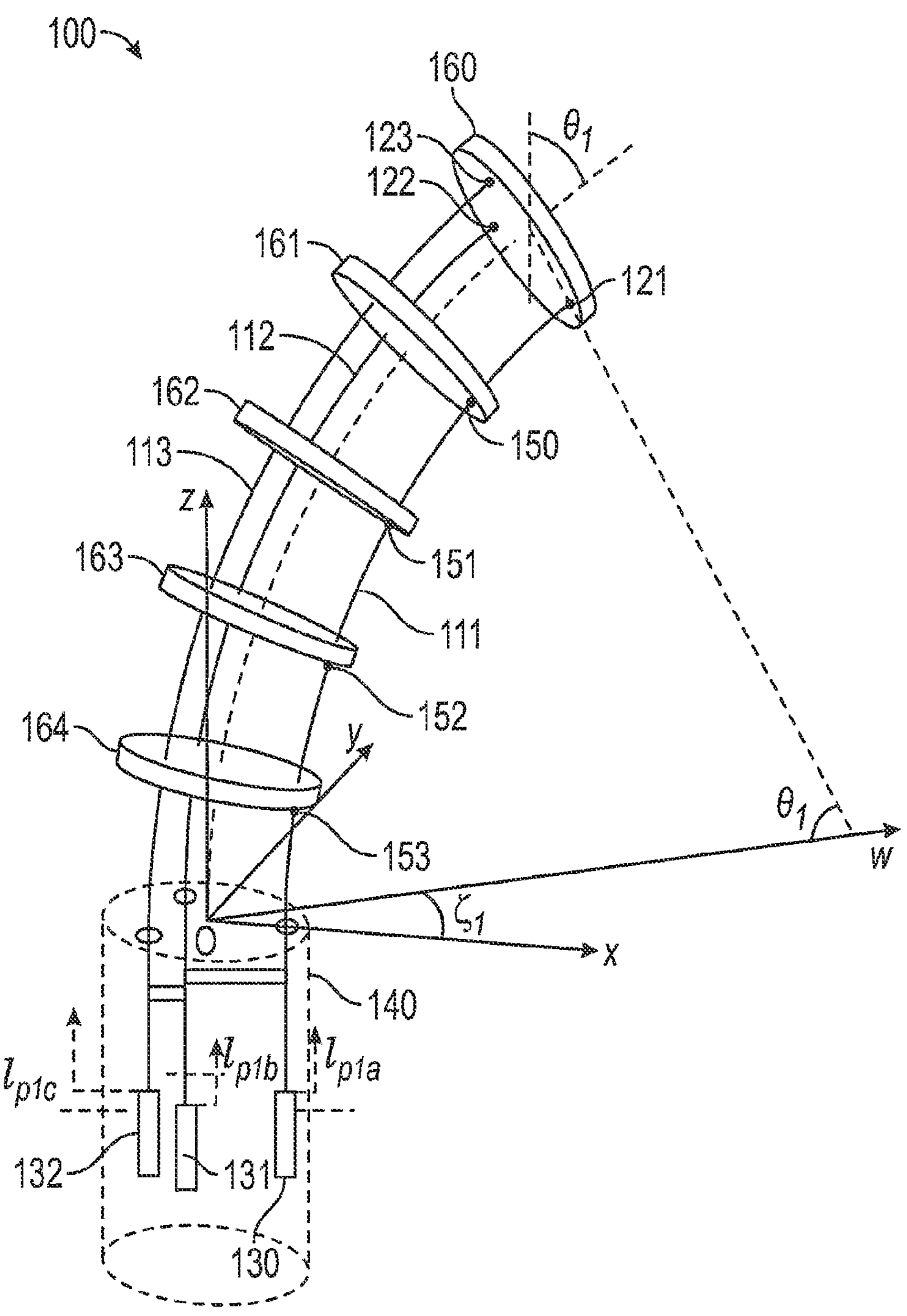
FIG. 2 is a diagram illustrating a kinematic model according to the first embodiment.

FIG. 1 illustrates a continuum robot including n bending sections (bending portions) used in this embodiment. The continuum robot is a bendable body, which is connected to a base and is capable of moving in the z-axis direction in addition to the bending operation. FIG. 2 illustrates a first bending section (a proximal bending portion) at the most proximal end in enlarged view. The posture of the continuum robot is controlled in such a way that wires 111 to 113 are connected to joint portions 121 to 123 at the distal end 160 of the bending sections and are pushed and pulled with actuators 130 to 132 installed in a robot base 140, respectively. The robot base 140 (hereinafter sometimes simply referred to as "base") is moved by an advance controller that performs control for advancing the continuum robot. The advance controller displaces the position of the base, so that the continuum robot moves forward and backward in the longitudinal direction.

In this embodiment, the three wires 111 to 113 serve as a driving mechanism (a second bending mechanism) for bending the proximal bending portion. The continuum robot of this embodiment further includes three wires as a driving mechanism (a first bending mechanism) for bending a bending section (a distal bending portion) at the distal end. The continuum robot according to this embodiment further includes three wires serving as a driving mechanism (a third bending mechanism) for the following bending portion following the distal bending portion. This embodiment is an example in which one bending portion is bent using three wires. However, the number of wires is not limited thereto. The continuum robot further includes wire guides 161 to 164 which are members for guiding the wires. The wire guides may be a plurality of discretely arranged members or an accordion or mesh-like continuum member. The wire guides may each have a through-hole in the center, through which an observation tool or another tool is to be passed. An example of the observation tool is a medical tool, such as an endoscope. Other examples of the tool include forceps, a biopsy needle, and a cautery tool. Observation using a continuum robot hereinafter refers to acquisition of images captured by an observation tool (an image capturing apparatus), such as an endoscope, passed through the continuum robot. Another example is acquisition of images using an image capturing apparatus incorporated as part of the continuum robot. Controlling the position and orientation of the distal end of the continuum robot according to this embodiment allows the image capturing direction of the observation tool to be oriented to a desired direction. The wire guides are fixed to the wire 111 at fixing portions 150 to 153. The central axis of the continuum robot is indicated by the broken line.

The continuum robot according to this embodiment further includes a controller for driving the wires 111 to 113 to bend the bending portions by controlling the actuators 130 to 132, respectively. The controller controls the continuum robot according to a command from a receiving unit (for example, a joystick) that receives a command on the curvature of part or all of the bending portions.

The control performed by the controller will be described hereinbelow. The controller controls a first driving mechanism to bend the distal bending portion. The controller controls a second driving mechanism to bend the proximal bending portion.

Figure 3:
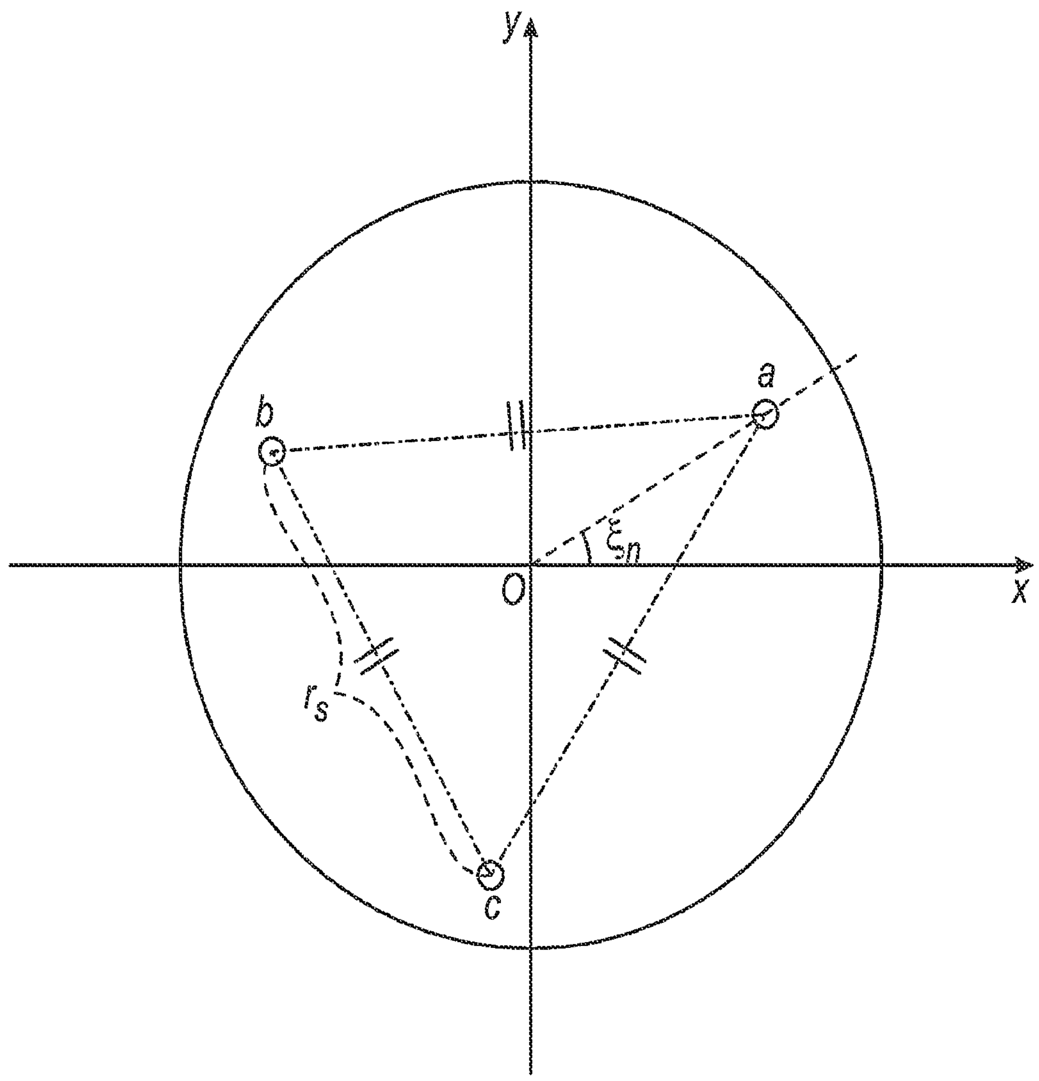
FIG. 3 is a diagram illustrating a kinematic model according to the first embodiment.

In this embodiment, the wires are referred to as wires a, b, and c in the counterclockwise direction in an x-y plane, and the respective displacements of the wires driven in the n-th bending section are referred to as $l_{pna}$, $l_{pnb}$, and $l_{pnc}$. FIG. 3 illustrates a circular surface of each of the wire guides 161 to 164. The three wires are individually arranged at the vertices of an equilateral triangle whose length is $r_s$ in the circular surface, as shown in FIG. 3, where phase angle $\xi_n$ is an angle that determines the placement of the wires that drive the n-th bending section.

Figure 6:
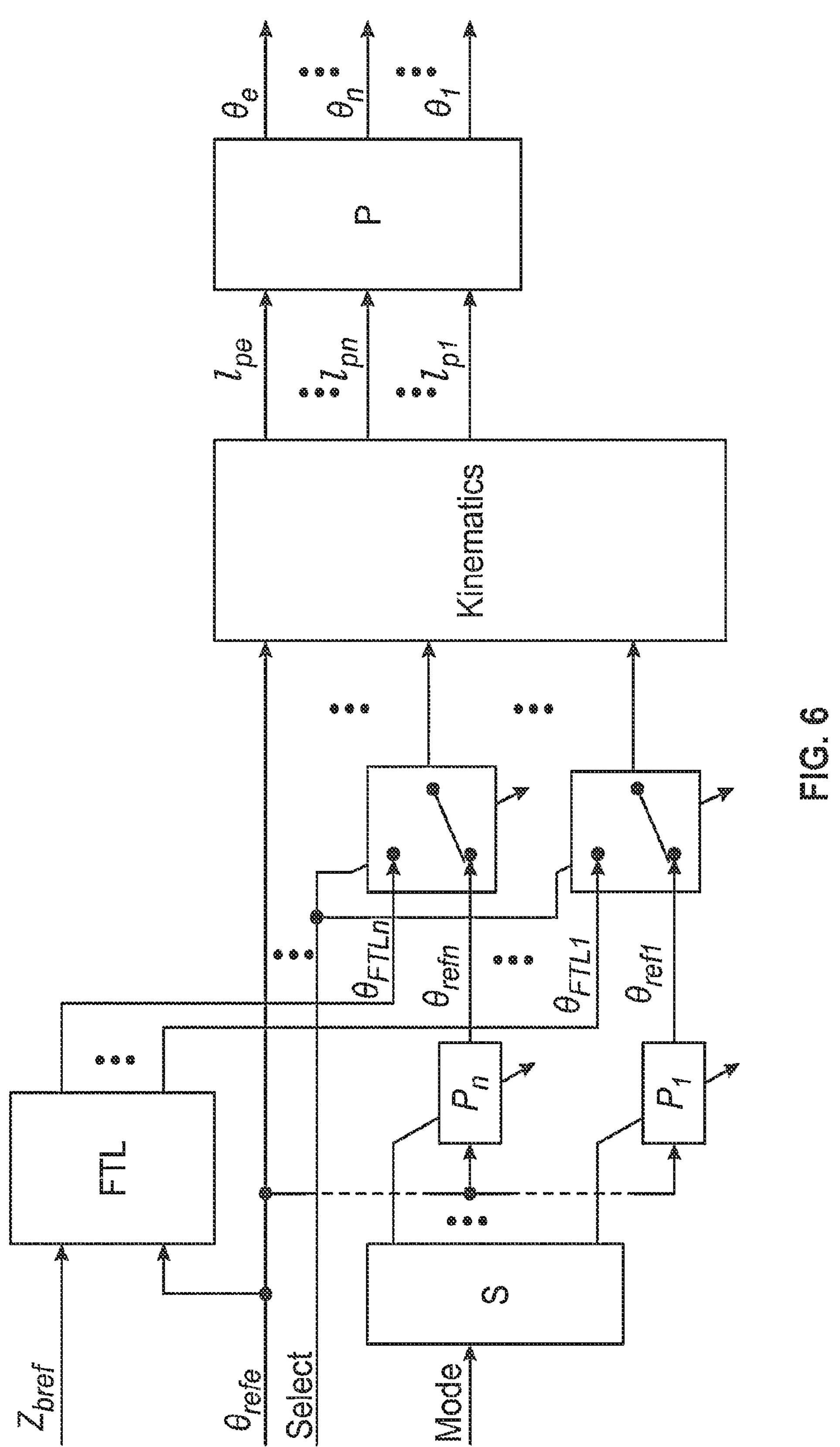
FIG. 6 is a diagram illustrating a control system according to the first embodiment.

In this embodiment, control in an x-z plane, with all phase angles set at $\xi_n=0$, will be first described. FIG. 6 is a block diagram of a control system for a continuum robot including e bending sections, in which $\theta_{refe}$ denotes the amount of operation on the most distal end performed by the operator, P denotes the continuum robot, and Kinematics is a block for calculating the kinematics. Block FTL is a block for operating a control algorithm for propagating the bent shape of the most distal end to the following portion (hereinafter referred to as "follow-the-leader control"). In the follow-the-leader control, when the continuum robot is advanced by an advance controller after the controller performs control for bending only the distal bending portion according to a received command, the controller performs control for automatically bending the following bending portion on the basis of the curvature of the distal bending portion that is bent according to the command.

The block constituted by block S and a parameter group $p_n$ (n=1, . . . , e−1) is a control system that enables operating the shape of the bending sections of the entire continuum robot only with a command on the amount of operation $\theta_{refe}$ by setting a target value $\theta_{refn}$ for the n-th bending section, obtained by multiplying the operating amount $\theta_{refe}$ by the parameter group $p_n$, as follows:

$$\theta_{refn} = p_n\theta_{refe} \;\; (n = 1, \ldots , e-1) \tag{1}$$

Furthermore, the operation mode of the continuum robot can be changed by replacing the parameter group $p_n$. Block S stores the values of the parameter group $p_n$ and sets the parameter group $p_n$ according to the operation mode command mode. The details of the operation mode will be described later. The operation mode can freely be changed by the operator. In this embodiment, this control system is referred to as "bent shape control". The operator can freely select the follow-the-leader control or the bent shape control by operating a switch Select.

Derivation of a kinematic model written as Kinematics and the control system described in blocks FTL, S, and $p_n$ will be described in detail below.

(1) Modeling

Derivation of kinematics of the continuum robot in an x-z plane will be described below.

Figure 4:
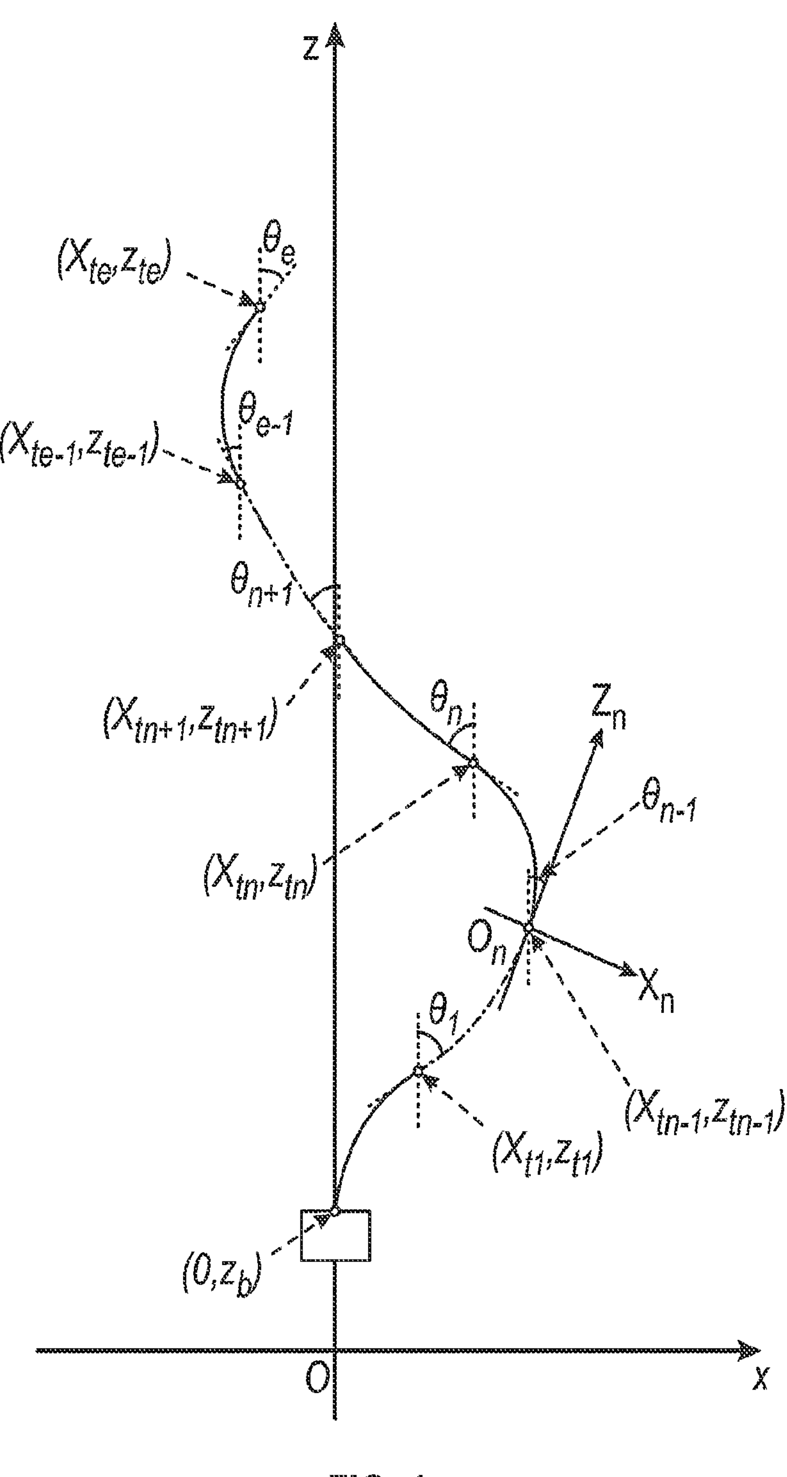
FIG. 4 is a diagram illustrating a kinematic model according to the first embodiment.
Figure 5:
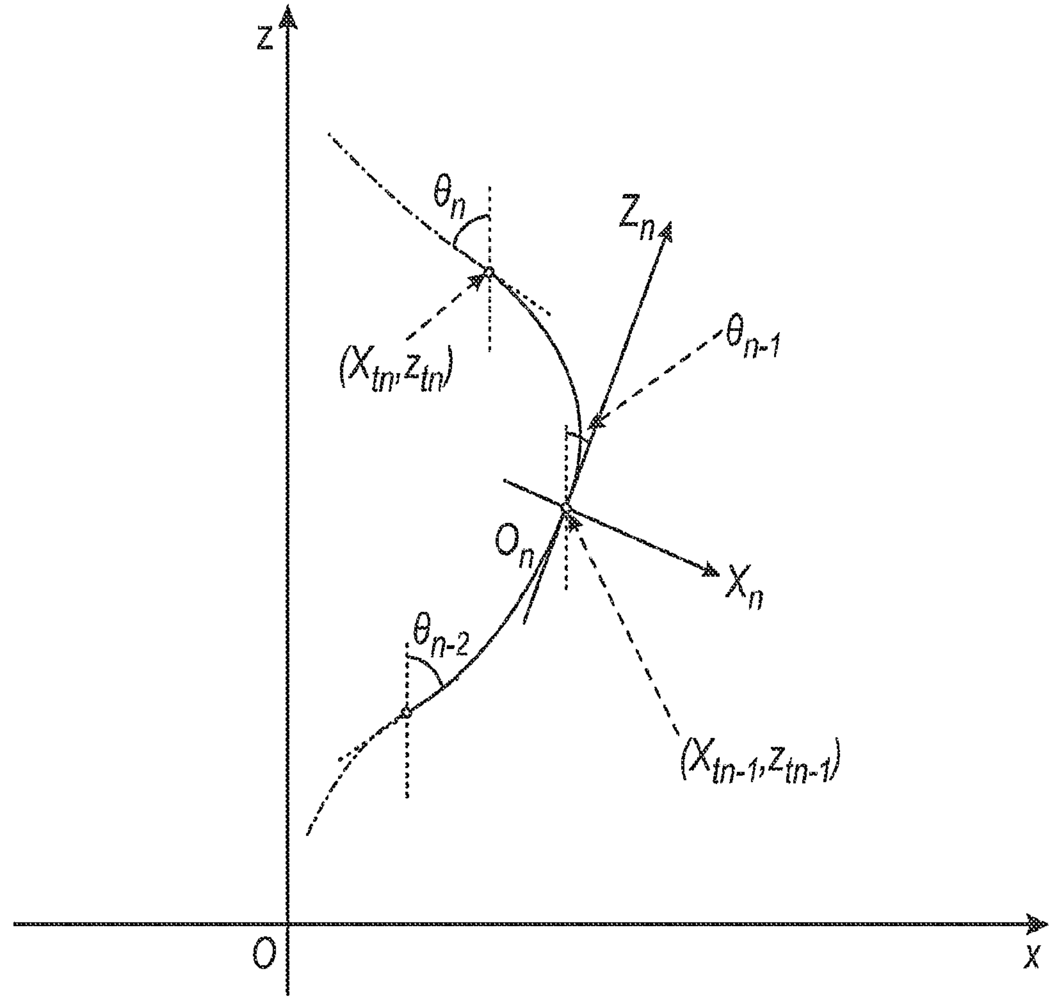
FIG. 5 is a diagram illustrating a kinematic model according to the first embodiment.

The definition of the signs is as follows: $l_n$ is the length of the n-th bending section, $r_n$ is the distance from a wire passing through the wire guide of the n-th bending section to the center of the wire guide, e is the number of bending sections of the robot, $\theta_n$ is the angle of the distal end of the n-th bending section, $\rho_n$ is the radius of curvature of the n-th bending section, $\theta_{refn}$ is the target angle of the distal end of the n-th bending section, $l_{pn}$ is the driven angle of a wire of the n-th bending section, $x_{tn}$ and $z_{tn}$ are the coordinates of the distal end of the n-th bending section, and $z_b$ is the displacement of the base. The kinematics of the continuum robot whose number of bending sections is shown in FIG. 4 is derived on the assumption as follow:

1. The wires are deformed only in an x-z plane.
2. The wires are deformed with a constant curvature in the individual bending sections.
3. The torsional deformation of the wires is not taken into account.
4. The wires are not deformed in the longitudinal direction.

First, only the first bending section will be discussed. If wire a is driven, and wires b and c are fixed, the relationship between the drive amount $l_{p1}$ of the wire and the angle $\theta_1$ of the distal end of the first bending section is given by $$l_{p1} = \frac{3}{2} r_1 \theta_1 \tag{2}$$

Next, the relationship between the wire drive displacement $l_{pn}$ and the angle $\theta_n$ of the distal end of the n-th bending section is derived. The bend relative angle $\tilde{\theta}_n$ of the n-th bending section is defined as follows:

$$\tilde{\theta}_n = \theta_n - \theta_{n-1} \tag{3}$$

where n is 2 or greater.

In the relative coordinate system $x_n$–$z_n$, in which the origin is at $x_{tn}$–1, $z_{tn}$–1, and which is formed by the $\theta_{n-1}$ direction and the direction orthogonal thereto, as shown in FIG. 4, the relationship between the wire drive displacement $\tilde{l}_{pn}$ and the angle $\tilde{\theta}_n$ of the distal end of the first bending section is given by $$\tilde{l}_{pn} = \frac{3}{2} r_n \tilde{\theta}_n \tag{4}$$

The wire drive displacement $l_{pn}$ of the n-th bending section is the sum of the displacements of the wires for driving the n-th bending section in the relative coordinate system from the first to (n–1)-th sections and is given by $$l_{pn} = \frac{3}{2} r_n \left(\tilde{\theta}_n + \tilde{\theta}_{n-1} + \ldots + \theta_1\right) = r_n \theta_n \tag{5}$$

This shows that the angle $\theta_n$ of the distal end of the n-th bending section depends only on the wire drive displacement $l_{pn}$ and does not depend on the angle of the intermediate bending sections.

Next, the relationship between the angle and the coordinates of the distal end of the n-th bending section is derived. First, the first bending section will be discussed.

$$x_{t1} = \frac{l_1}{\theta_1}(1 - \cos\theta_1) \tag{6}$$

$$z_{t1} = \frac{l_1}{\theta_1}\sin\theta_1 \tag{7}$$

Next, the relationship between the angle and the coordinates of the distal end of the n-th bending section is derived. The coordinates $\tilde{x}_{tn}$, $\tilde{z}_{tn}$ of the distal end of the bending section in the relative coordinate system $x_n$–$z_n$ is given by $$\tilde{x}_{tn} = \frac{l_n}{\tilde{\theta}_n}\left(1 - \cos\tilde{\theta}_n\right) \tag{8}$$

$$\tilde{z}_{tn} = \frac{l_n}{\tilde{\theta}_n}\sin\tilde{\theta}_n \tag{9}$$

where n is 2 or greater.

Thus, the coordinates $x_{tn}$, $z_{tn}$ of the distal end in the absolute coordinate system is given using a rotational transform matrix as follows:

$$\begin{bmatrix} x_{tn} \\ z_{tn} \end{bmatrix} = \begin{bmatrix} x_{t1} \\ z_b + z_{t1} \end{bmatrix} + \sum_{m=2}^{n} \begin{bmatrix} \cos\theta_{m-1} & \sin\theta_{m-1} \\ -\sin\theta_{m-1} & \cos\theta_{m-1} \end{bmatrix} \begin{bmatrix} \frac{l_m}{\tilde{\theta}_m}\left(1 - \cos\tilde{\theta}_m\right) \\ \frac{l_m}{\tilde{\theta}_m}\sin\tilde{\theta}_m \end{bmatrix} \tag{10}$$

(2) Designing Control System (2.a) Follow-the-Leader Control

Figure 7:
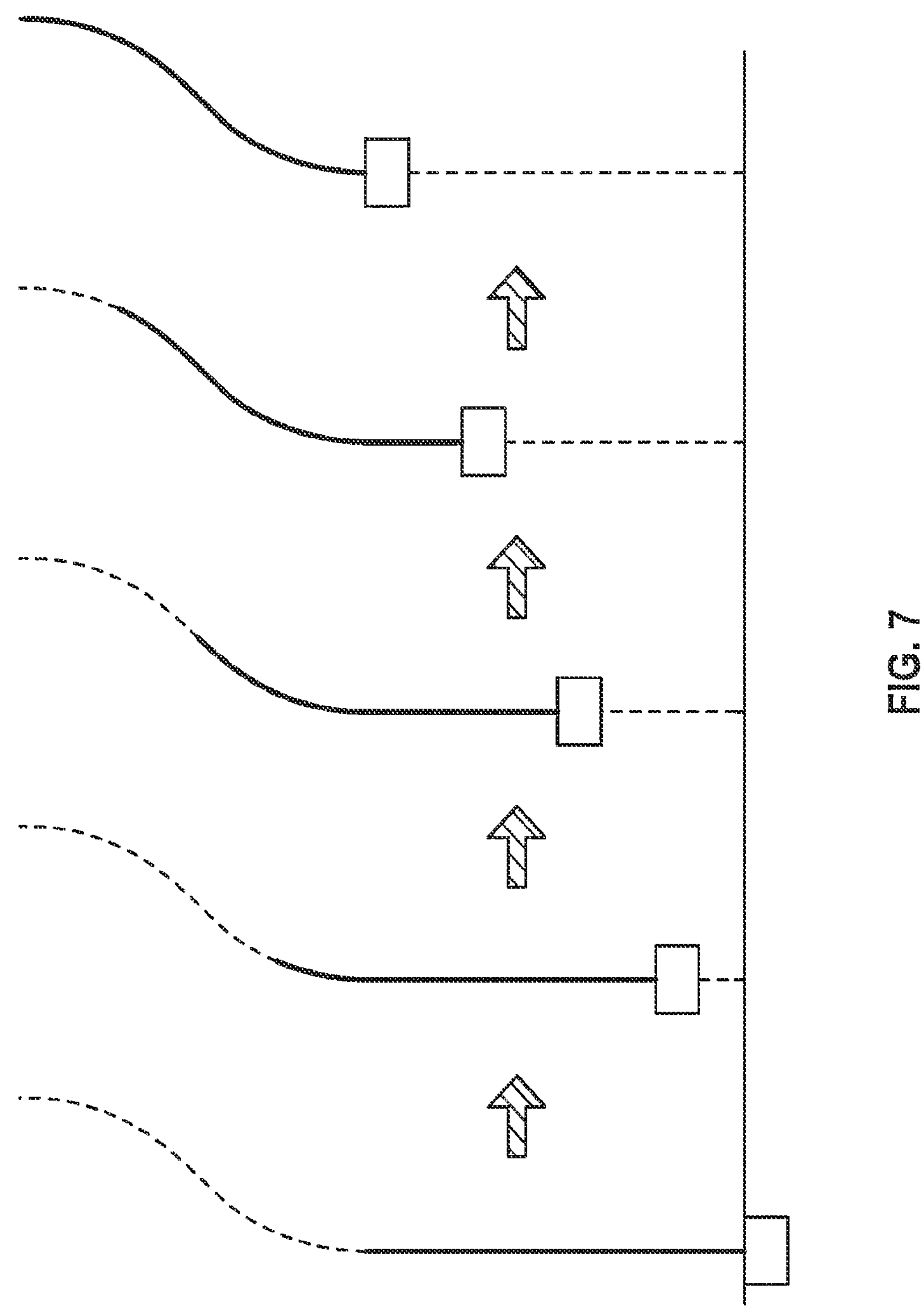
FIG. 7 is a diagram illustrating follow-the-leader control according to the first embodiment.

The follow-the-leader control is a method of control so that the trailing bending sections (following bending portions) pass through the same path through which the bending section at the most distal end (distal bending portion) passes, as shown in FIG. 7. This allows the continuum robot to advance through a small space. The follow-the-leader control does not necessarily need to determine the path in advance and need only propagate the bending angle of the most distal end to the following bending sections across the length of the bending sections. The use of this method allows the operator to perform follow-the-leader control of the continuum robot in actual time by giving commands on only the bending angle of the most distal end and the amount of advance of the base with a joystick or the like.

Figure 8:
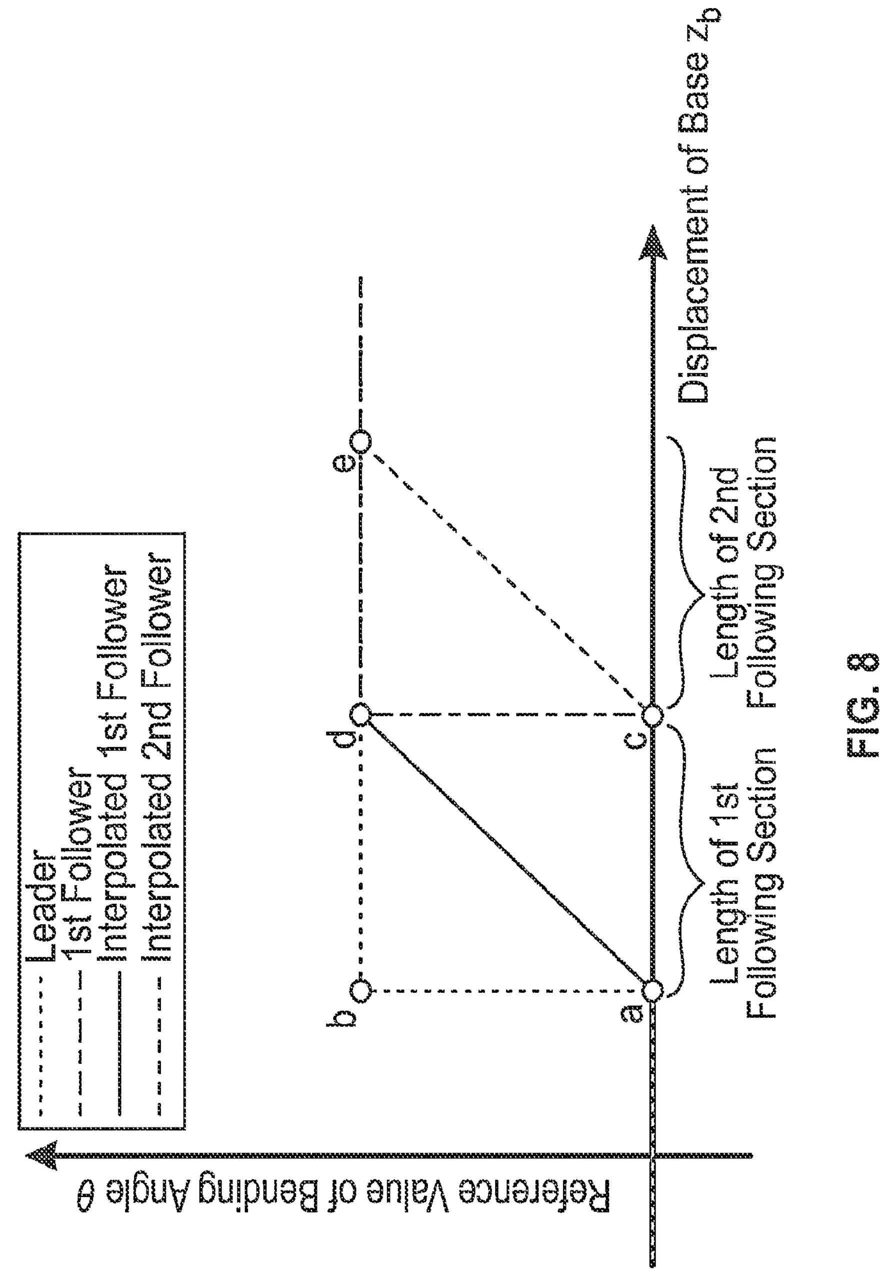
FIG. 8 is a graph illustrating follow-the-leader control according to the first embodiment.

FIG. 8 shows a graph with base displacement $z_b$ on the horizontal axis and bending angle $\theta$ on the vertical axis. The dotted line indicates a bending command of the operator to the most distal end, and the thick broken line indicates a bending command on the first following bending section. When a bending angle command ab is given at base displacement a by the operator, the following bending angle cd is automatically generated at base displacement c. The base displacement c is determined so that the distance ac takes a bending section length of 1. The following bending angle command is stored in a storage of a control operation apparatus and is drawn out according to the base displacement. However, with this command value, since the first following bending angle does not change when the base displacement is a or c, and a bending angle command for the following bending section rises at base displacement c, the continuum robot exhibits an abrupt behavior. For this reason, this embodiment interpolates the angle command for the first following bending section so as to connect point a and point d. The interpolated target angle of the first following bending section is indicated by the solid line in FIG. 8. When the number of bending sections is 2 or more, the first following section in the foregoing description is replaced with the most distal end, and this process is performed continuously. This allows the bending angle command values for all the bending sections to be obtained. A bending angle command for the second following bending section is indicated by the thin broken line by way of example.

(2.b) Bent Shape Control

This chapter describes a method for designing the parameter group $p_n$ for achieving, as bent shape control, three bending modes, (A) a tip bending mode, B) a constant-curvature bending mode, and (C) a proximal bending mode.

(A) Tip Bending Mode

In the tip bending mode, only the bending section at the distal end is bent. Parameter group $p_n$ is written as:

$$p_n = 0 (n = 1, \ldots, e-1) \tag{11}$$

(B) Constant-Curvature Bending Mode

In the constant-curvature bending mode, the parameter group $p_n$ is set so that the curvature is constant over the entire bending portion of the continuum robot including a plurality of bending sections. If the length of the n-th bending section is $l_n$, the ratio to the length le of the bending section at the distal end is $l_n$/le. Accordingly, to make the curvature of the continuum robot constant, the ratio of the relative angle θ~e of the bending section at the distal end to the relative angle $\theta^{-}_{n}$ of the n (n=1, . . . , e−1)-th bending section is set to 1: $l_n/l_e$. The relationship between the target value $\theta^{-}_{refe}$ of the relative angle of the bending section at the distal end and the target value $\theta_{refe}$ of the absolute angle is expressed as:

$$\frac{l_1}{l_e}\tilde{\theta}_{refe} + \frac{l_2}{l_e}\tilde{\theta}_{refe} + \ldots + \tilde{\theta}_{refe} = \frac{l_1 + l_2 + \ldots + l_e}{l_e}\tilde{\theta}_{refe} = \theta_{refe} \tag{12}$$

Thus, $$\tilde{\theta}_{refe} = \frac{l_e}{\sum_{k=1}^{e} l_k}\theta_{refe} \tag{13}$$

Thus, the target value $\theta_{refn}$ of the absolute angle of the n-th bending section is written as, $$\theta_{refn} = \frac{l_1}{l_e}\tilde{\theta}_{refe} + \frac{l_2}{l_e}\tilde{\theta}_{refe} + \ldots + \frac{l_n}{l_e}\tilde{\theta}_{refe} = \frac{\sum_{k=1}^{n} l_k}{\sum_{k=1}^{e} l_k}\theta_{refe} \tag{14}$$

Thus, parameter $p_n$ is given by $$p_n - \frac{\sum_{k=1}^{n} l_k}{\sum_{k=1}^{e} l_k}(n - 1, \ldots, e - 1) \tag{15}$$

(C) Proximal Bending Mode

In the proximal bending mode, the first bending section follows the target angle for the operating amount $\theta_{refe}$, and the target values of the relative angles of the second—to (e-1)-th bending sections are set to 0. This can be achieved by making the target values of all the bending sections equal to the target value of the absolute angle of the distal end. Thus, the parameter group $p_n$ is written as:

$$p_n = 1(n = 1, \ldots, e - 1) \tag{16}$$

(3) Simulation

Figure 9A:
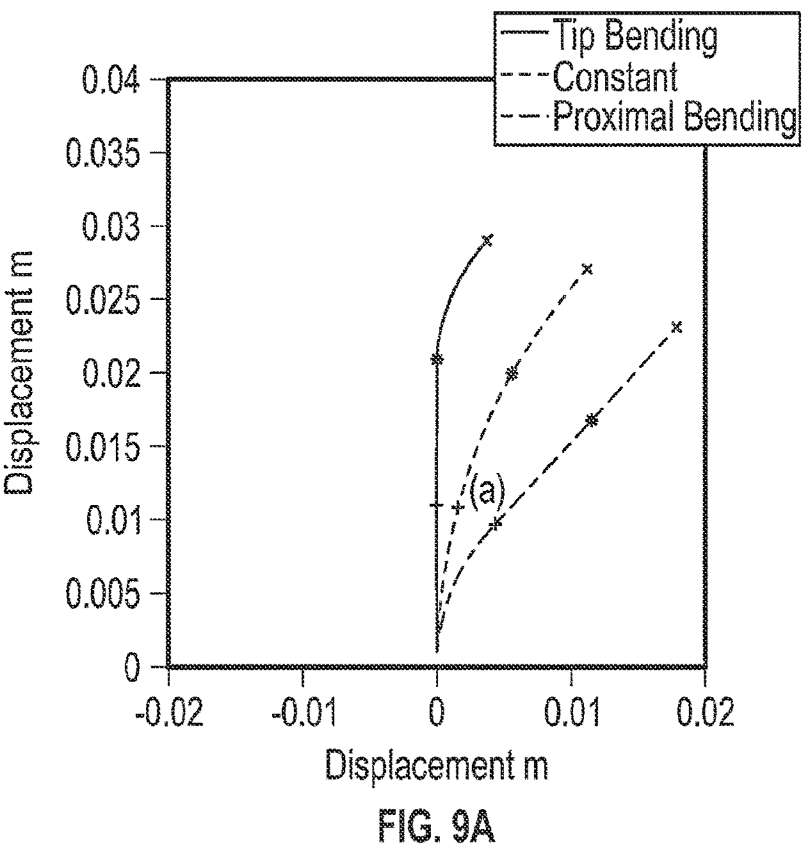
FIGS. 9(*a*) and 9(*b*) are graphs illustrating simulation results according to the first embodiment.
Figure 9B:
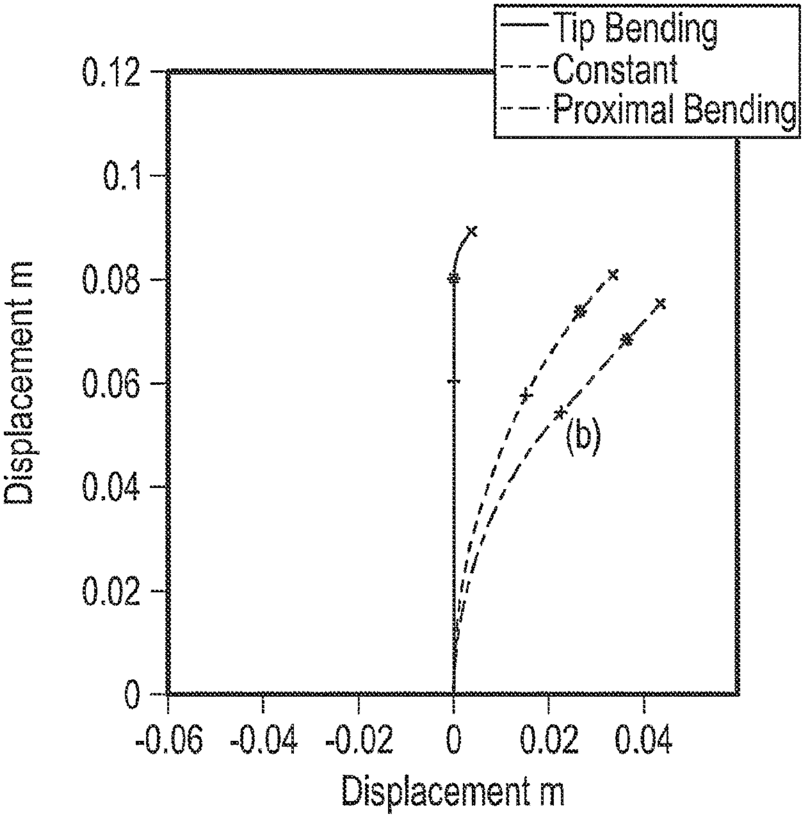

FIG. 9(*a*) illustrates responses of the individual operation modes in bent shape control of the continuum robot. In one example, the number of bending sections is set to 3, and all of the lengths of the bending sections are set to 0.010 m. The target angle of the third section is set to 45 degrees, and the bent shapes in the tip bending mode, the constant-curvature bending mode, and the proximal bending mode are indicated by the solid line, the broken line, and the dashed-dotted line, respectively. The coordinates of the distal ends of the first, second, and third bending sections are indicated by mark +, *, and X, respectively. The variation range of the x coordinate of the distal end relative to the operating amount of the operator increases in the order of the tip bending mode, the constant-curvature bending mode, and the proximal bending mode in order from the smallest variation range. The increase in the variation range allows wide-range observation, for example, observation with an observation tool inserted in the continuum robot. However, if an obstacle or the like is present in the vicinity of the proximal end, the proximal bending mode has a high risk that the obstacle comes into contact with the bending portion. FIG. 9(*a*) shows that control using the constant-curvature bending mode has a lower risk of contact with obstacles in the vicinity of the proximal end than the risk in control using the proximal bending mode and allows wider-range observation than observation using the tip bending mode.

FIG. 9(*b*) shows the bent shapes in the individual operation modes in the continuum robot in which the lengths of the first to third bending sections are 0.060 m, 0.020 m, and 0.010 m, respectively. For example, the number of bending sections is set to three. The target angle of the third section is set to 45 degrees, and the bent shapes in the tip bending mode, the constant-curvature bending mode, and the proximal bending mode are indicated by the solid line, the broken line, and the dashed-dotted line, respectively. The coordinates of the distal ends of the first, second, and third bending sections are indicated by mark +, *, and X, respectively. The shape in the constant-curvature bending mode, indicated by the broken line, shows that the curvature of the entire continuum robot can be made constant using the parameter calculation algorithm described in the foregoing chapter. This shows that the constant-curvature bending mode enables both of reduction in the risk of contact with obstacles in the vicinity of the proximal end and wide-range observation, as in the case where the lengths of all the bending sections are equal, shown in FIG. 9(*a*).

Figures 10A, 10B, 10C, 10D, 10E:
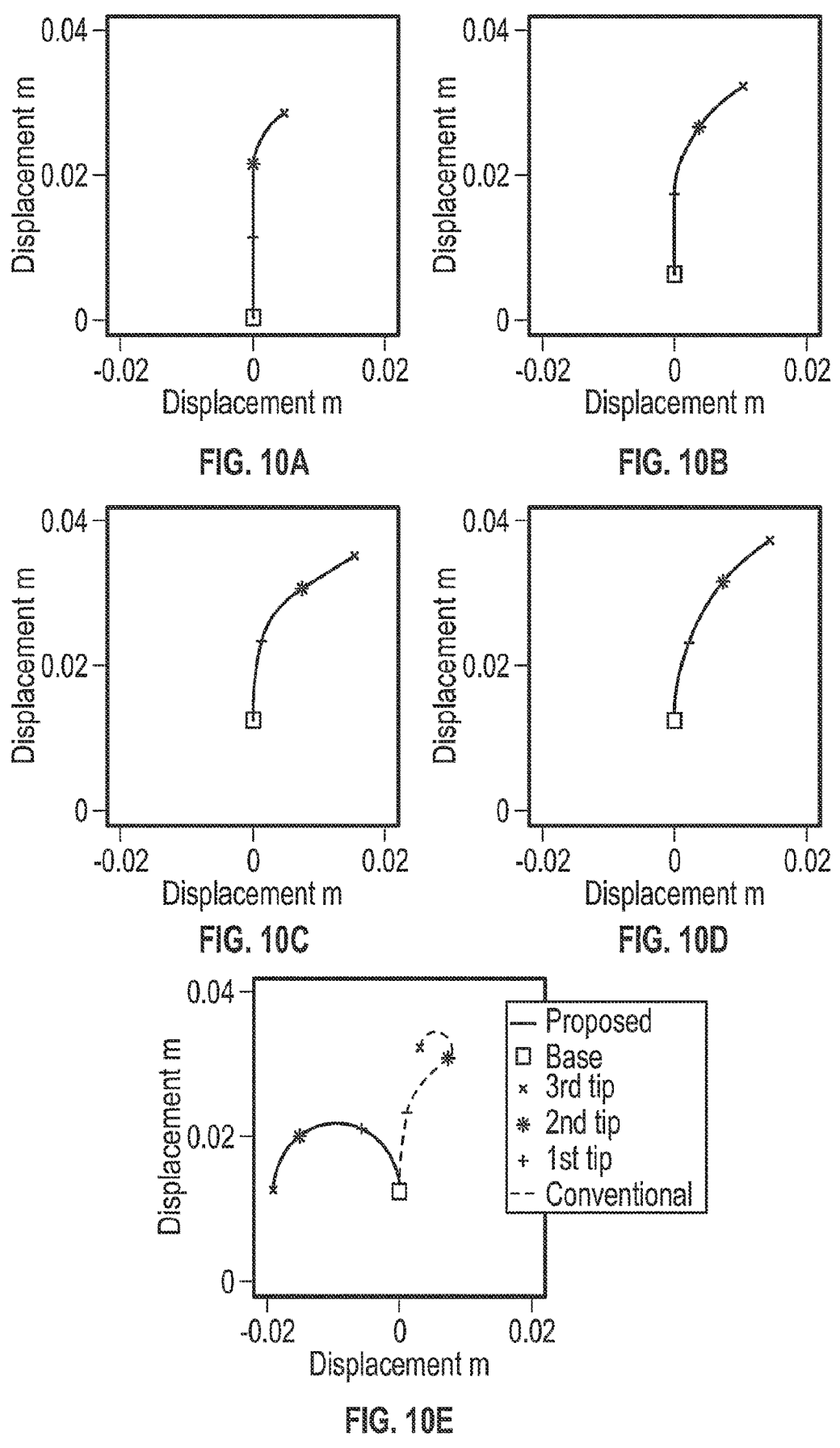

Next, FIGS. 10(*a*) to 10(*e*) show responses of a simulation in which the follow-the-leader control is switched to the bent shape control. At the start of the follow-the-leader control, the base is advanced as in FIGS. 10(*b*) and 10(*c*) from the state in which the bending angle $\theta_3$ of the most distal end is 45 degrees, as shown in FIG. 10(*a*). In FIG. 10(*d*), the advance of the base is stopped, and the mode is switched to the constant-curvature bending mode of the bent shape control. FIG. 10(*e*) shows a response of the operator changing the target angle to bend the bending angle $\theta_3$ of the most distal end to −180 degrees. For comparison, the broken line indicates a response of changing the bending angle $\theta_3$ of only the most distal end to −180 degrees, the follow-the-leader control kept. The broken line shows that the distal end can move in the wider range than the solid line. In other words, by switching to the bent shape control, the moving range (flexibility) of the distal end can be increased as compared with a case where the follow-the-leader control is continued. In other words, with the observation operation in the case where the follow-the-leader control is continued, wide-range observation increases the curvature of the bent shape of the distal end to increase the load on the continuum robot mechanism or to cause the continuum robot itself to block the field of view. In contrast, by switching the mode from the follow-the-leader control to the bent shape control, wide-range observation can be performed while the curvature of the distal end of the continuum robot is kept small as compared with the follow-the-leader control.

This embodiment allows the user to control the bending of the continuum robot by switching the three bending modes, as bent shape control modes, (A) tip bending mode, (B) constant-curvature bending mode, and (C) proximal bending mode, according to the object.

In the tip bending mode, only the bending section at the distal end of the continuum robot bends, which can reduce or eliminate the bending of the entire continuum robot. Accordingly, this allows the position of the distal end to be moved while preventing the continuum robot from coming into contact with a tube through which the continuum robot is passed (for example, the trachea or the intestinal tract).

In the proximal bending mode, the proximal end of the continuum robot is bent, which can significantly change the position of the distal end of the continuum robot. In other words, bending the bending section at the proximal end can move the distal end in a wider range than that when physically or mechanically bending the bending section at the distal end to the maximum.

In the constant-curvature mode, the range in which the position of the distal end of the continuum robot can be changed is wider than the range in the tip bending mode. Furthermore, this can reduce the risk of the continuum robot coming into contact with the tube through which the continuum robot is passed as compared with the proximal bending mode.

Thus, the controller according to this embodiment can perform first control (control with the tip bending mode) for bending only the distal bending portion according to a command that the receiving unit received. The controller according to this embodiment can also perform second control (constant-curvature bending mode) for bending the distal bending portion and the proximal bending portion so that the curvature of the distal bending portion and the curvature of the proximal bending portion become constant according to a command received by the receiving unit. The controller according to this embodiment can also perform third control (control using the proximal bending mode) for bending only the proximal bending portion according to a command received by the receiving unit. The controller according to this embodiment can control the continuum robot by switching between the first control and the second control. The controller according to this embodiment can also control the continuum robot by switching among the first control, the second control, and the third control.

According to this embodiment, the user can switch control of the continuum robot from the follow-the-leader control to the bent shape control. By switching to the bent shape control, the moving range (flexibility) of the distal end can be increased as compared with a case where the follow-the-leader control is continued.

According to this embodiment, even while controlling only the distal bending portion, such as follow-the-leader control, the operator can directly or easily control the overall shape or partial shape of the continuum robot and can switch to an operation for linking the plurality of bending sections.

Second Embodiment

A second embodiment is an example in which the bent shape control described in the first embodiment is applied to the start of the follow-the-leader control.

(1) Designing Control System

Figure 11:
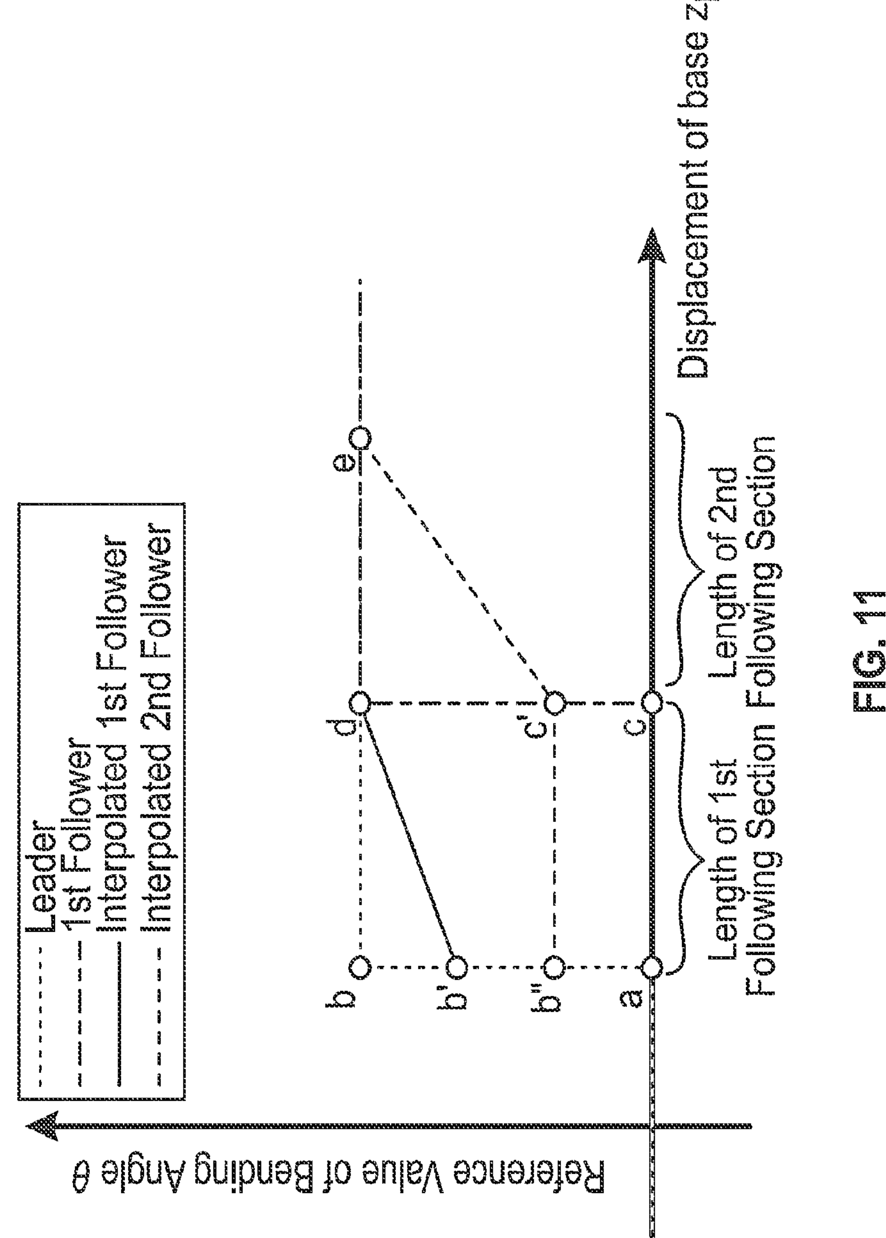
FIG. 11 is a graph illustrating follow-the-leader control according to a second embodiment.
Figure 12:
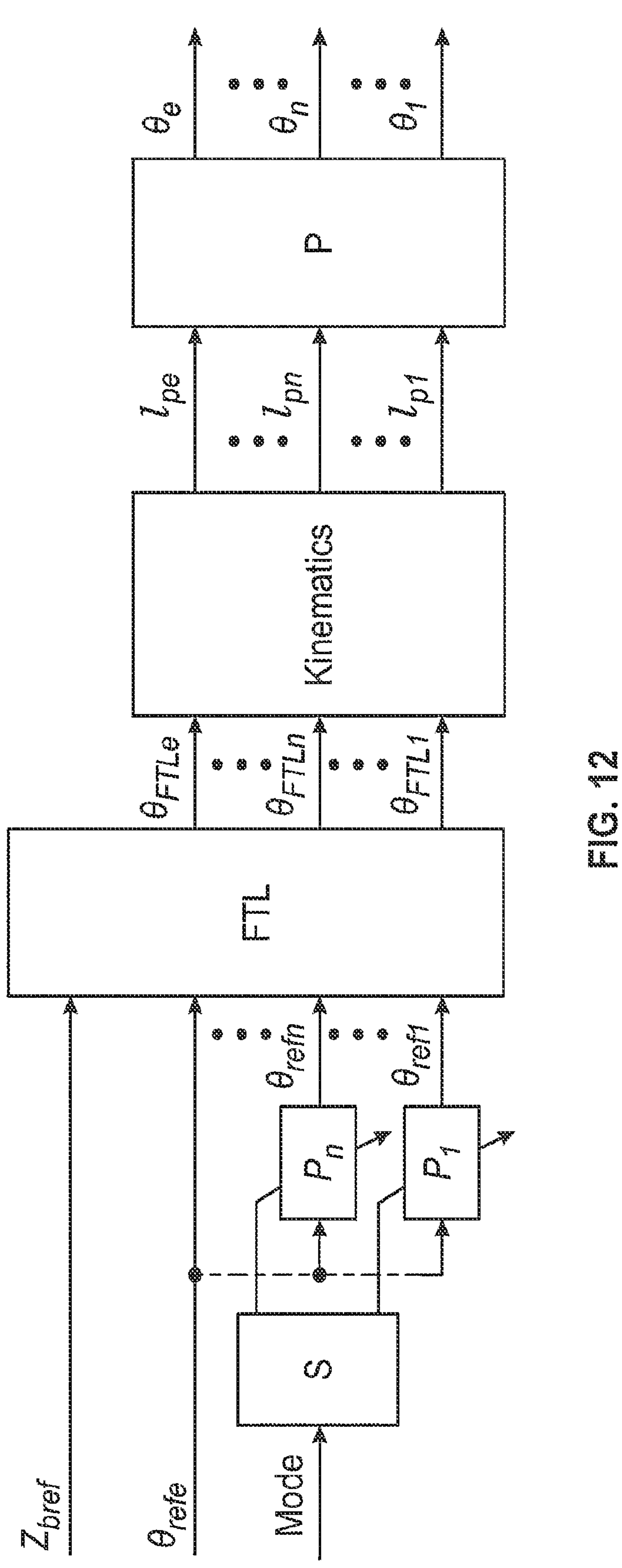
FIG. 12 is a diagram illustrating a control system according to the second embodiment.

In this embodiment, the constant-curvature bending mode is used as the operation mode of bent shape control, and after a bending operation, the follow-the-leader control is started. A method for generating target angles for the following bending sections will be described. FIG. 11 shows a graph in which the dotted line indicates a bend command for the most distal end to the operator, and the solid line and the broken line respectively indicate bend commands for the first and second following bending sections, as in the first embodiment in FIG. 8. In one example, assume that the lengths of all the bending sections are equal. When bending angle command ab is given at base displacement a by the operator, bending angle command ab' and bending angle command ab" are given to the first and second following bending sections, respectively, on the basis of the algorithm shown in the first embodiment. The angle command for the first following bending section is generated so as to connect point b' and point d, as indicated by the solid line in FIG. 11. The angle command for the second following bending section is generated so as to keep bending angle command ab" until base displacement c at which base displacement $z_b$ exceeds the length of the first bending section, and after the base displacement c, so as to connect point c' and point e, as indicated by the broken line in FIG. 11. FIG. 12 illustrates a block diagram of this control system.

(2) Simulation

Figures 13A, 13B, 13C, 13D, 13E:
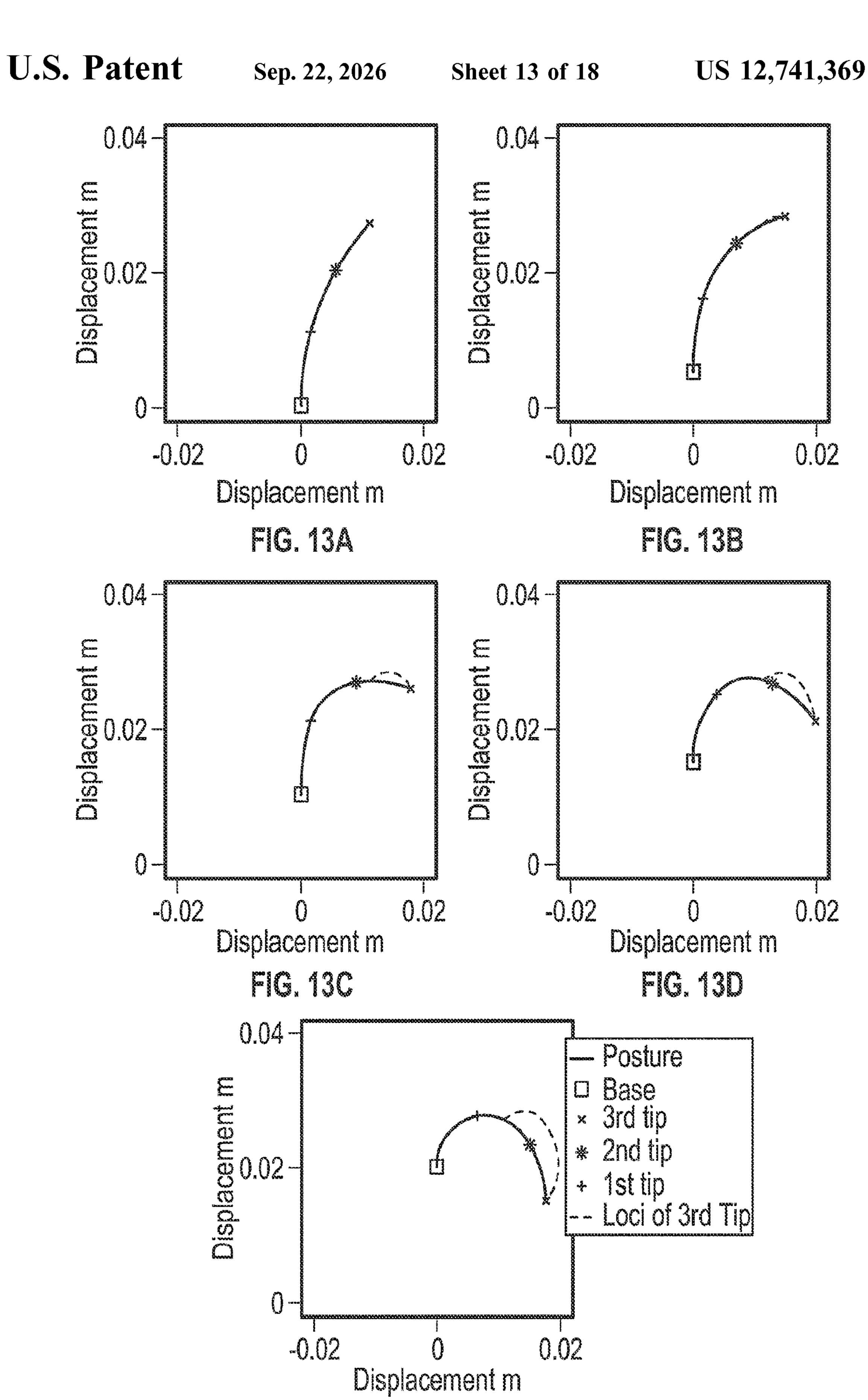
FIGS. 13(*a*) to 13(*e*) are graphs illustrating simulation results according to the second embodiment.

FIGS. 13(*a*) to 13(*e*) show responses of a simulation in which follow-the-leader control is started after an operation for the most distal end using the constant-curvature bending mode. In one example, the number of bending sections is set to 3, and all of the lengths of the bending sections are set to 0.010 m. The bending angles $\theta_3$ of the most distal end at the start and the end of the follow-the-leader control are set to 45 degrees and 180 degrees, respectively, and the base is advanced by 0.020 m while the angles are continuously changed. The shape of the continuum robot is indicated by the solid line. The coordinates of the distal ends of the first, second, and third bending sections are indicated by mark +, *, and X, respectively. The displacement of the base is indicated by an unfilled square mark. The locus of the most distal end due to the follow-the-leader control is indicated by the broken line. The base is advanced as shown in FIGS. 13(*b*) to 13(*d*) from the constant-curvature bending state shown in FIG. 13(*a*), and in FIG. 13(*d*), the bending angle $\theta_3$ of the distal end reaches 180 degrees. At that time, no abrupt change occurred in the curvature of the locus of the most distal end. This is because starting the follow-the-leader control from the constant-curvature bending mode, as shown in FIG. 11, decreases the change in the angle of the following bending sections.

Figures 14A, 14B, 14C, 14D, 14E:
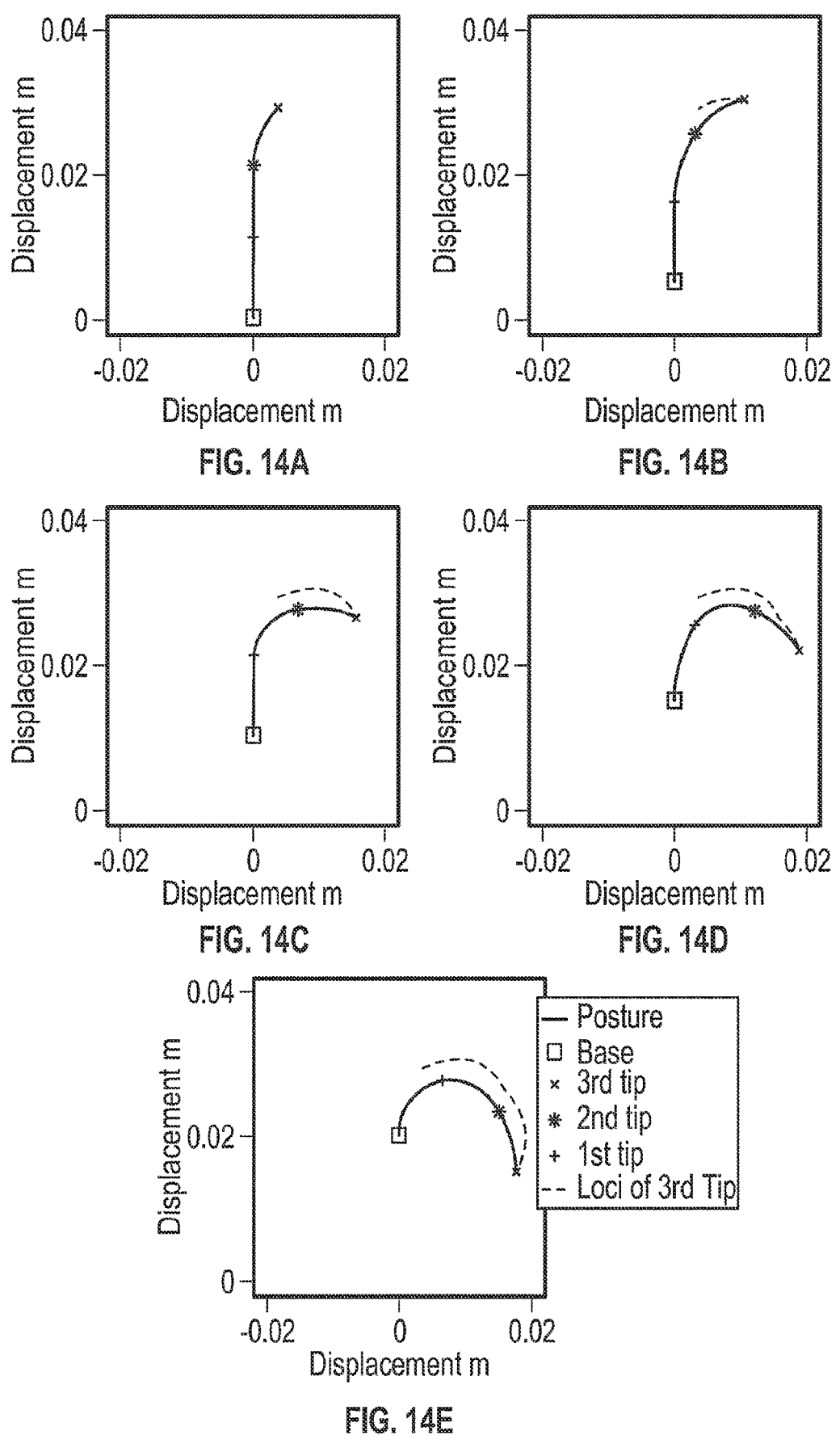
Figure 15:
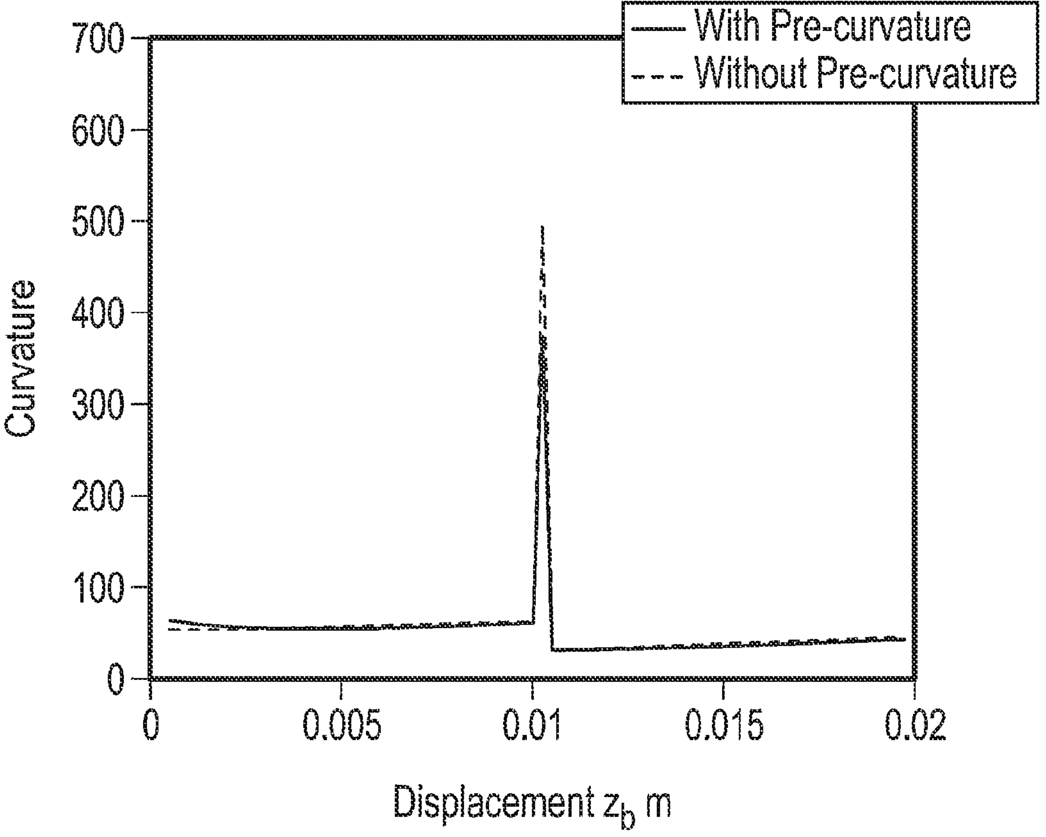
FIG. 15 is a graph illustrating simulation results according to the second embodiment.

For comparison, FIGS. 14(*a*) to 14(*e*) show responses of a simulation with only the follow-the-leader control. Conditions for the simulation are the same as those in FIG. 13. FIGS. 14(*c*) to 14(*e*) show that the locus of the most distal end abruptly changes in curvature at the start of the bending o the first bending section. This is because the change in the angles of the following bending sections is larger than that at when the follow-the-leader control is started from the bent shape control. FIG. 15 shows the curvature response of the locus of the most distal end relative to the base displacement. The response when the follow-the-leader control is started from the constant-curvature bending mode is indicated by the solid line, and the curvature response with only the follow-the-leader control is indicated by the broken line for comparison. This shows that the control system of this embodiment reduces changes in the locus curvature in the vicinity of a base displacement of 0.01 m.

Thus, starting the follow-the-leader control from the constant-curvature bending mode allows stable operation without causing an abrupt change in the field of view of the operator.

Third Embodiment

Figure 16:
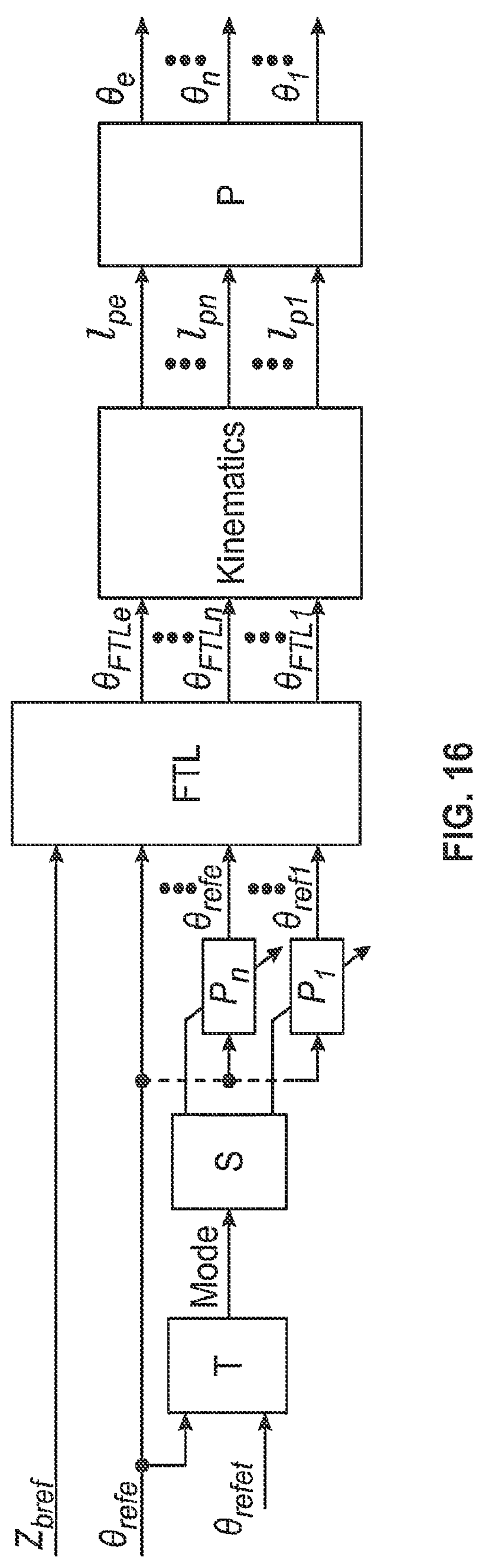
FIG. 16 is a diagram illustrating a control system according to a third embodiment.

In the second embodiment, the bent shape at the start of the follow-the-leader control is selected by the operator. However, the locus of the most distal end changes depending the target bending angles at the start and the end of the follow-the-leader control. For this reason, abrupt changes in the locus can be reduced at not all of the target bending angles. For this reason, this embodiment additionally includes a determination block T in the control system, as shown in FIG. 16. The operator gives a final value $\theta_{refet}$ of the operating amount to the determination block T in addition to the operating amount $\theta_{refe}$ of the most distal end. The determination block T calculates the locus of the most distal end involving the advance of the base using the kinematics described in the first embodiment and stores the maximum value of the curvature. The storage stores the maximum value of the curvature of the distal bending portion when the distal end of the distal bending portion is advanced for a certain section by the follow-the-leader control. By comparing the maximum values of the curvature using and not using the bent shape control before starting the follow-the-leader control, the determination block determines whether to use the bent shape control before the start of the follow-the-leader control.

Figure 17:
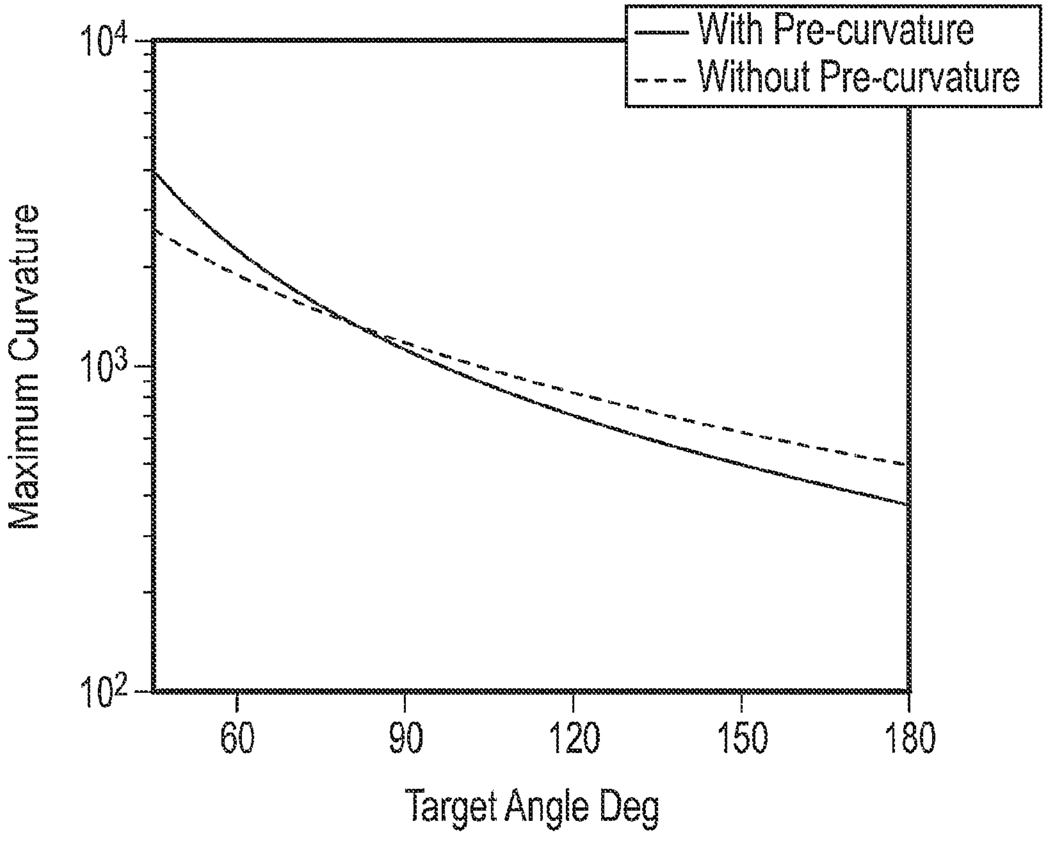
FIG. 17 is a graph illustrating simulation results according to the third embodiment.

FIG. 17 shows responses of a simulation. This plots the maximum curvature of the locus of the most distal end in a simulation in which the operating amount increases with the advance of the base when the operating amount $\theta_{refe}$ of the most distal end changes from 45 degrees at the start of the follow-the-leader control to 180 degrees at intervals of 5 degrees. A response with the control of this embodiment is indicated by the solid line, and a response with only the follow-the-leader control is indicated by the broken line. The variation range of the bending angle of the most distal end increases in the range in which the final value is about 80 degrees or more. The curvature change can be reduced by starting the follow-the-leader control from the constant-curvature bending mode. In contrast, the angles at the start and the end of the follow-the-leader control do not significantly differ in the range from 45 degrees to about 80 degrees. For this reason, the use of only the follow-the-leader control can decrease the curvature change of the locus. Thus, comparing the maximum curvatures of the locus of the most distal end allows reducing the abrupt change of the locus at all the target bending angles.

In this embodiment, when the maximum value stored in the storage exceeds a predetermined value (for example, 80 degrees), the controller starts the follow-the-leader control after performing control (second control) with the constant-curvature bending mode. If the maximum value stored in the storage is the predetermined value or less, the controller performs control to start the follow-the-leader control without performing the control using the constant-curvature bending mode.

Fourth Embodiment

The first to third embodiments show changing the operation mode of the robot in an x-z plane and a follow-the-leader control using it. This embodiment performs shape control in a three-dimensional space.

To find the drive displacements of the actuators for controlling the bending angle and the rotation angle of the continuum robot, kinematics are derived. The following signs are defined, in addition to the signs defined in the first embodiment. $\xi n$ is the rotational angle of the n-th bending section, and $\xi refn$ is the target rotational angle of the n-th bending section. Assuming the following conditions, and the kinematics of the continuum robot is derived.

1. The wires are deformed with a constant curvature in the individual bending sections.
2. The torsional deformation of the wires is not taken into account.
3. The wires are not deformed in the longitudinal direction.
4. The friction between each wire guide and the wires is not taken into account.

First, the relationship among the drive displacement lp1a, lp1b, and lp1c of the wires a, b, c, the bending angle $\theta 1$ and the rotational angle $\xi 1$ of the distal end of the first bending section is written as:

$$
\begin{aligned}
l_{p1a} &= \frac{r_s}{\sqrt{3}}\cos\zeta_1\theta_1 \\
l_{p1b} &= \frac{r_s}{\sqrt{3}}\cos\left(\frac{\pi}{6}+\zeta_1\right)\theta_1 \\
l_{p1c} &= \frac{r_s}{\sqrt{3}}\cos\left(\frac{\pi}{6}-\zeta_1\right)\theta_1
\end{aligned} \tag{17}
$$

Next, the relationship among the drive displacements $l_{pna}$, $l_{pnb}$, and $l_{pnc}$ of the wires a, b, and c and the bending angle $\theta_n$ and the rotational angle $\xi_n$ of the distal end of the continuum robot including a plurality of bending sections is found. The phase angle $\xi_n$ of each wire that drives the n-th bending section is written as:

$$
\xi_n = \frac{120}{e}n \tag{18}
$$

where e is the number of bending sections.

Thus, the wire drive displacements $l_{pna}$, $l_{pnb}$, and $l_{pnc}$ of the n-th bending section are expressed as:

$$
\begin{aligned}
l_{pna} &= \frac{r_s}{\sqrt{3}}\cos(\zeta_n-\xi_n)\theta_n \\
l_{pnb} &= \frac{r_s}{\sqrt{3}}\cos\left(\frac{\pi}{6}+\zeta_n-\xi_n\right)\theta_n \\
l_{pnc} &= \frac{r_s}{\sqrt{3}}\cos\left(\frac{\pi}{6}-\zeta_n+\xi_n\right)\theta_n
\end{aligned} \tag{19}
$$

Figure 18:
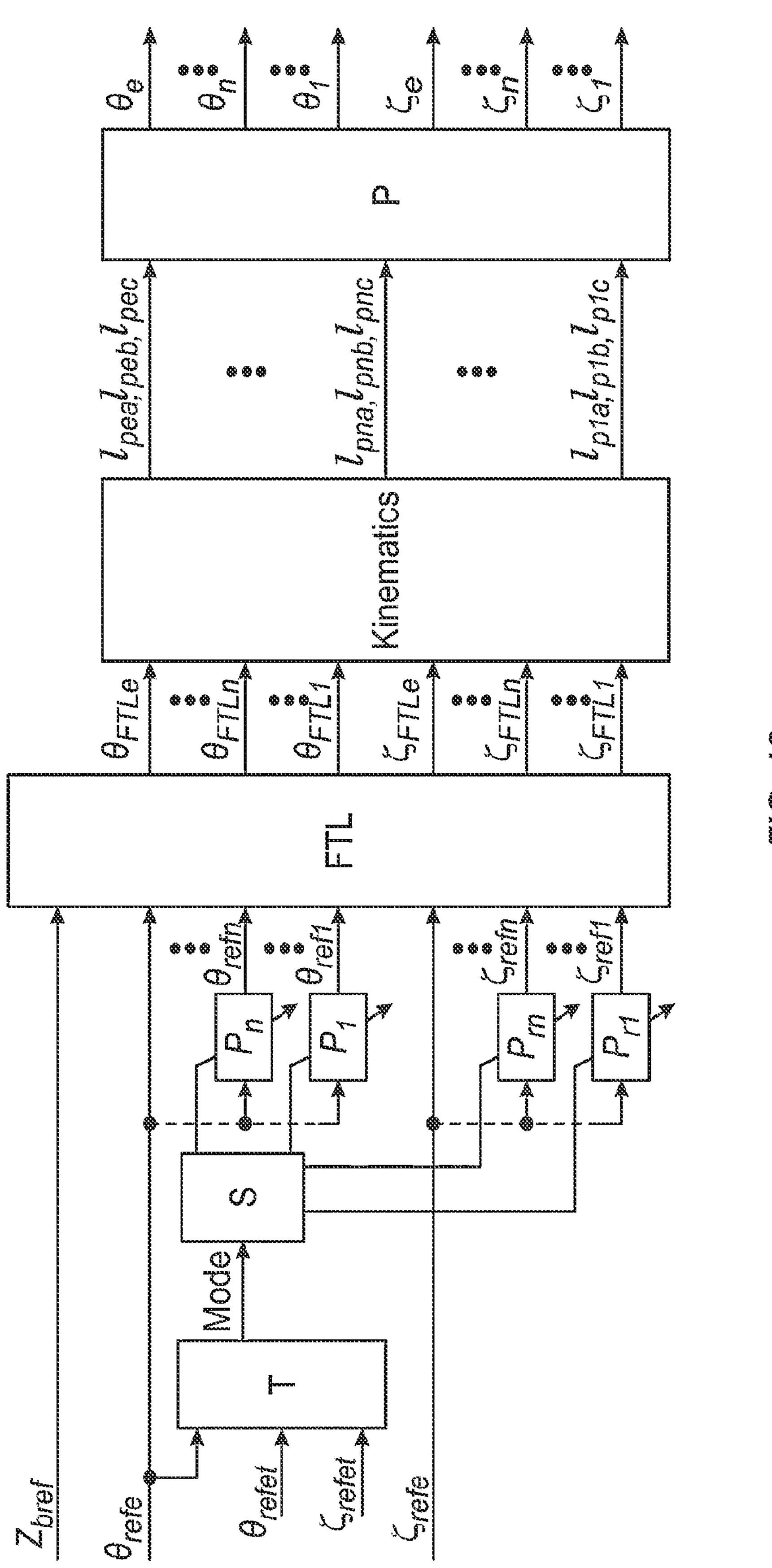
FIG. 18 is a graph illustrating a control system for changing the operation mode in the three-dimensional space according to a fourth embodiment.

Next, bent shape control in the three-dimensional space is designed. FIG. 18 illustrates a control system for changing the operation mode in the three-dimensional space, where prn is a parameter group that determines the rotational angle of the n-th bending section. In the constant-curvature bending mode and the proximal bending mode, the target rotational angles of all the bending sections are set equal to the target rotational angle $\xi refe$ of the most distal end. Thus, in the tip bending mode, the parameter group of the rotational angle is expressed as:

$$
prn = 0,\ (n = 1, \ldots, e-1) \tag{20}
$$

For the constant-curvature bending mode and the proximal bending mode, the parameter group is expressed as:

$$
prn = 1,\ (n = 1, \ldots, e-1) \tag{21}
$$

To start the follow-the-leader control after the bent shape control, the bending target angle is given an initial value, and then the bending angle of the distal end is propagated to the following sections, as in the second embodiment of the plane drive, and the target angle is calculated using a similar algorithm in which the bending angle in the second embodiment is replaced with the rotational angle. Thus, the follow-the-leader control in the three-dimensional space can be performed by obtaining a wire drive displacement for each of the following bending sections using Equation (19). In the operation-mode determination block T, the locus of the most distal end may be calculated as in the third embodiment using the final value $\theta_{refet}$ of the operating amount of the bending angle, or the final value $\xi_{refet}$ of the operating amount of the rotational angle may be added for evaluation.

The invention claimed is:

1. An apparatus comprising:

a bendable body including at least a first bending portion and a second bending portion;

a first driving mechanism for bending the first bending portion;

a second driving mechanism for bending the second bending portion;

a controller that controls the first driving mechanism to bend the first bending portion and controls the second driving mechanism to bend the second bending portion;

a receiver that receives a command on an amount of bending of part or all of the bending portions, an advance controller that performs control for advancing the bendable body, and a storage that stores a maximum amount of bending of the first bending portion in a case where a distal end of the first bending portion is advanced for a certain section by the follow-the-leader control, wherein the controller is configured to switch between first control for bending the first bending portion according to the command received by the receiver and second control for bending the first bending portion and the second bending portion so that the first bending portion and the second bending portion have constant curvature according to the command received by the receiver, wherein, when the controller performs first control for bending the first bending portion according to the command and the bendable body is advanced by the advance controller, the controller performs follow-the-leader control for automatically bending a bending portion following the first bending portion based on the amount of bending of the first bending portion bent according to the command, and wherein, when the maximum amount stored by the storage exceeds a predetermined value, the controller starts the follow-the-leader control after performing the second control, and in a case where the maximum amount stored by the storage is the predetermined value or less, the controller performs control for starting the follow-the-leader control without performing the second control.

2. The apparatus according to claim 1, wherein the bending portion includes the first bending portion, the second bending portion, and a third bending portion, and wherein the bending portion following the first bending portion is the third bending portion, wherein the first bending portion is a distal bending portion, the second bending portion is a proximal bending portion and the third bending portion is a middle bending portion which is between the distal bending portion and the second bending portion.

3. The apparatus according to claim 1, wherein the bending portion following the first bending portion is the second bending portion.

4. The apparatus according to claim 1, wherein the controller is configured to switch among a control for bending the second bending portion, the first control, and the second control according to the command received by the receiver.

5. A system comprising:

a continuum robot including a plurality of bending sections driven with a wire;

a driver that drives the wire;

a base-stage controller on which the continuum robot is mounted and which is configured to move the continuum robot in a longitudinal direction; and a robot controller including a first controller that controls a driving amount of the wire based on a kinematics operator that associates an angle of a distal end of the continuum robot and the driving amount of the wire, a second controller that determines an angle of a distal end of a following bending section from an angle of a distal end of a leading bending section and a displacement of the base stage, and a first operator that gives an angle command to the leading bending section and a displacement command to the base stage, wherein the robot controller further includes a third controller that receives the angle command output from the first operator and operates an angle command for the following bending section using a parameter group; and a storage that stores the parameter group, wherein the parameter group is selected by a second operator and is sent from the storage to the third controller, wherein the angle command for the following bending section can be selected by switching between an output from the second controller and an output from the third controller.

6. The system according to claim 5, wherein the angle command calculated by the third controller is used as an initial value for the second controller.

7. The continuum robot according to claim 6, wherein the robot controller comprising at least one processor and at least one memory that stores instructions, wherein the instructions is executed by the at least one processor to perform:

receiving a last angle of the angle of the distal end of the leading bending section and a last displacement of the base stage;

calculating a locus of the distal end of the leading bending section using a kinematic model of the continuum robot;

obtaining a maximum value of a curvature distribution of the locus;

changing a displacement of the base stage;

storing a maximum value of a curvature distribution caused by displacement of the base stage; and searching for another parameter group in which the maximum value of the curvature distribution caused by the displacement of the stage is smallest by executing replacement of the parameter group, input with the receiving, calculation with the calculating, acquisition with the obtaining, and storage with the storing.

* * * * *